United States Patent [19]

Gervais

[11] Patent Number: 4,754,037
[45] Date of Patent: Jun. 28, 1988

[54] PROCESS FOR PREPARING N-METHYL DERIVATIVES OF ERGOLINE

[75] Inventor: Christian Gervais, Villeurbanne, France

[73] Assignee: Rhone-Poulenc Sante, Courbevoie, France

[21] Appl. No.: 884,043

[22] Filed: Jul. 10, 1986

[30] Foreign Application Priority Data

Jul. 11, 1985 [FR] France ................. 85 10620

[51] Int. Cl.$^4$ .......................................... C07D 457/04
[52] U.S. Cl. ........................................ 546/69; 546/67; 546/68
[58] Field of Search ............................. 546/67, 68, 69

[56] References Cited

U.S. PATENT DOCUMENTS 3,218,323 11/1965 Hofmann et al. ............... 546/68
3,228,943 1/1966 Bernardi et al. ............... 546/68
3,272,823 9/1966 Arcamone et al. ............. 546/69
3,879,554 4/1975 Temperilli .................... 546/69
4,232,157 11/1980 Enrico ........................... 546/68

FOREIGN PATENT DOCUMENTS 631701 11/1961 Canada ........................... 546/69
100569 12/1964 Denmark ........................ 546/69
0000533 7/1979 European Pat. Off. .
2116548 9/1983 United Kingdom .............. 546/68

OTHER PUBLICATIONS

Romano et al., CA 94–65300h, Aromatic Alkyl Amines.
Merger et al., CA 88–37405d, Aralkylarylamines and Alkylarylamines.
Societa Farmaceutici Italia, CA 61–3160, New Derivatives of Lumilysergol.
Maffrand et al., CA 96–199659g, Indolizeno 28, 7–63, Indole Derivatives, Intermediates, and Their Therapeutic Use.
Reinecke et al, J. Org. Chem., vol 37, No. 20, 1972, The Effect of Solvent and Cation on the Reaction of Organometallic Derivatives of Indole with Methyl Iodide.

Primary Examiner—Donald G. Daus
Assistant Examiner—Cecilia Shen
Attorney, Agent, or Firm—Stevens, Davis, Miller & Mosher

[57] ABSTRACT

A process for preparing an N-methyl derivative of ergoline of formula:

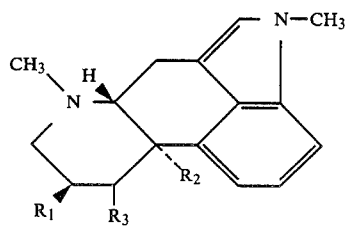

in which $R_1$ denotes a carboxy or alkoxycarbonyl group in which the alkyl portion contains 1 to 4 carbon atoms, $R_2$ denotes a hydrogen atom or a methoxy group and $R_3$ denotes a hydrogen atom or $R_2$ and $R_3$ together form a direct bond, or in which $R_1$ denotes a hydroxymethyl group, $R_2$ denotes a hydrogen atom or a methoxy group and $R_3$ denotes a hydrogen atom, which comprises methylating an ergoline derivative of formula:

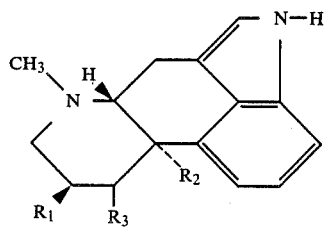

in which $R_1$, $R_2$ and $R_3$ are defined as above, with methyl carbonate in the presence of a basic agent, in an apolar aprotic solvent in the present of a phase transfer catalyst.

8 Claims, No Drawings

PROCESS FOR PREPARING N-METHYL DERIVATIVES OF ERGOLINE

The present invention relates to a process for preparing N-methyl derivatives of ergoline.

These compounds are useful intermediates for preparing compounds which have pharmacological activity, such as peripheral and cerebral vasodilators (nicergoline) or migraine prophylactics (methysergide, metergoline).

It is generally known to carry out the methylation of an indole ring-system, with a methyl halide or dimethylsulphate, in the presence of a base which is an alkali metal hydroxide or a hydride, amide or alcoholate or organometallic derivative such as an organomagnesium or organolithium derivative (see M. G. Reinecke, J. Org. Chem., 37 (20) 3066 (1972)). However, this technique does not give satisfactory results when the indole ring-system bears nitrogen-containing or hydroxyl substituents.

French Patent No. 1,359,563 describes the methylation of the nitrogen atom of the ergoline ring system by the action of a methyl halide in liquid ammonia in the presence of metallic potassium.

German Patent Application Nos. 2,618,033 and 3,007,196 described the methylation of an aniline using methyl carbonate at a temperature of from 180° to 250° C. or using methyl carbonate and methyl iodide at a temperature in the region of 150° C.

French Patent Application No. 2,478,639 describes the methylation of one particular indole derivative, 1-(2-(3-indolyl)ethyl)-2-pyrrolidone, using methyl carbonate in the presence of sodium hydride, the mixture being heated for 6 hours to the reflux temperature of tetrahydrofuran. However, the application of this process to the methylation of ergoline derivatives does not leed to satisfactory results.

The present invention provides a process for the preparation of an N-methyl derivative of ergoline of formula:

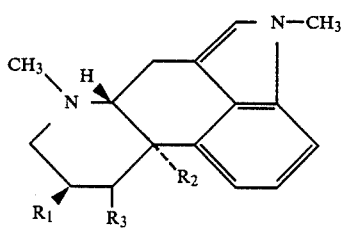
(I)

in which $R_1$ denotes a carboxy or alkoxycarbonyl group in which the alkyl portion contains 1 to 4 carbon atoms, $R_2$ denotes a hydrogen atom or a methoxy group and $R_3$ denotes a hydrogen atom or $R_2$ and $R_3$ together from a direct bond, or in which $R_1$ denotes a hydroxymethyl group. $R_2$ denotes a hydrogen atom or a methoxy group and $R_3$ denotes a hydrogen atom, which comprises methylating an ergoline derivative of formula:

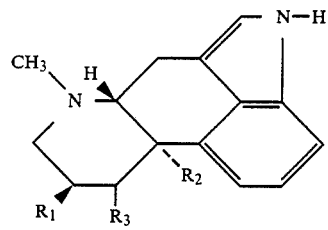
(II)

in which $R_1$, $R_2$ and $R_3$ are defined as above, with methyl carbonate in the presence of a basic agent such as an alkali metal hydride or alcoholate, for example sodium or potassium hydride or alcoholate, in an apolar aprotic solvent in the presence of a phase transfer catalyst, such as a quaternary ammonium salt, for example tetrabutylammonium chloride, and optionally in the presence of a sequestering agent such as a crown ether or a compound of formula:

$$N(CH_2CH_2(OCH_2CH_2)_nOCH_3)_3$$

wherein n is 1, 2 or 3.

The reaction is generally carried out at a temperature of from 0° to 100° C., preferably from 40° to 60° C.

Ethers, esters, nitriles or aromatic hydrocarbons are examples of compounds which can be used as apolar aprotic solvents. The process can be carried out in methyl carbonate itself, which therefore acts as both the methylating agent and the solvent and which, as a result of its relatively low boiling point (90° C.), can be readily removed.

The process according to the invention enables the methylation reaction to be carried out under mild conditions, using compounds which can be more readily handled than other methylating agents such as methyl halides and dimethyl sulphate. Methyl carbonate is, in particular, much less toxic.

When the ergoline ring-system is substituted with a tertiary amine or primary alcohol group, the side reactions which occur with the other known methylating agents, such as quaternization of the tertiary amine or etherification of the primary alcohol, do not generally take place. However, if the ergoline ring-system is substituted with a primary alcohol group it can be advantageous to treat the reaction product with a base such as sodium hydroxide before isolating the final product.

When the ergoline ring-system is substituted with an ester group, especially a methyl ester group, the group is prevented from undergoing a saponification reaction due to the conditions in which the process according to the invention is carried out.

The example which follow show how the invention may be put into practice.

EXAMPLE 1

A solution of methyl 10α-methoxylumilysergate (314 mg; $10^{-3}$ mol) in methyl carbonate (25 cc) was poured into a reactor containing sodium methylate (16×$10^{-3}$ mol) and tetrabutylammonium chloride (1.75×$10^{-3}$ mol).

The reaction mixture, maintained shielded from moisture, was stirred for 24 hours at a temperature in the region of 20° C.

Assay of the reaction mixture by high performance liquid chromatography showed that it contained methyl N-methyl-10α-methoxylumilysergate (0.8×10⁻³ mol).

The degree of conversion was 97%.

EXAMPLE 2

Tetrabutylammonium chloride (1.5 mmol) and sodium methylate (24 mmol) was added successively to a solution of methyl 10α-methoxylumilysergate (943 mg; 3 mmol) in methyl carbonate (100 cc).

The reaction mixture, maintained shielded from moisture, was stirred for 3 hours 30 minutes at 60° C. The reaction mixture then contained methyl N-methyl-10α-methoxylumilysergate (2.83 mmol), which corresponded to a 94% yield.

The degree of conversion of the methyl 10α-methoxylumilysergate was 98.5%.

Acetic acid (24 mmol) was added to the reaction mixture, which was then filtered on silica. The methyl N-methyl-10α-methoxylumilysergate, the characteristics of which were confirmed by proton nuclear magnetic resonance and high performance liquid chromatography, was thereby isolated.

EXAMPLE 3

10α-Methoxylumilysergol (268 mg; 1 mmol) was suspended in a mixture (30 cc) of methyl carbonate and tetrahydrofuran (1:1 by volume). Sodium methylate (8 mmol) and tetrabutylammonium chloride (2 mmol) were then added. The reaction mixture was stirred for 5 hours at 60° C. The solvents were evaporated off under reduced pressure and a methanol/water (4:1 by volume) mixture (30 cc) was then added. The aqueous methanolic solution was heated to 60° C. for 3 hours.

N-Methyl-10α-methoxylumilysergol was isolated after precipitation by adding water at a temperature in the region of 10° C.

The yield of N-methyl-10α-methoxylumilysergol was 96%.

The degree of conversion of the 10α-methoxylumilysergol was 98%.

The structure of the product obtained was confirmed by nuclear magnetic resonance and high performance liquid chromatography.

EXAMPLE 4

The procedure of Example 2 was repeated, but using:
methyl 10αmethoxylumilysergate: 1 mmol methyl carbonate: 8 cc tetrabutylammonium chloride: 0.02 mmol sodium methylate: 8 mmol After heating for 22 hours at 60° C., methyl N-methyl-10α-methoxylumilysergate (0.72 mmol) was formed in a 72% yield.

I claim:

1. A process for preparing an N-methyl compound of ergoline of formula:

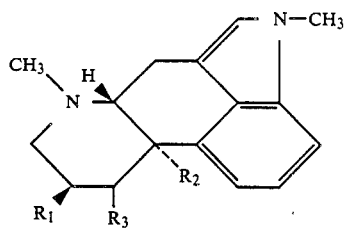

in which $R_1$ denotes a carboxy or alkoxycarbonyl group in which the alkyl portion contains 1 to 4 carbon atoms, $R_2$ denotes a hydrogen atom or a methoxy group and $R_3$ denotes a hydrogen atom or $R_2$ and $R_3$ together form a direct bond, or in which $R_1$ denotes a hydroxymethyl group, $R_2$ denotes a hydrogen atom or a methoxy group and $R_3$ denotes a hydrogen atom, which comprises methylating an ergoline compound of formula:

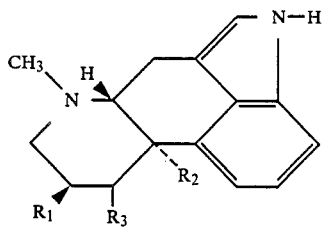

in which $R_1$, $R_2$ and $R_3$ are defined as above, with methyl carbonate in the presence of an alkali metal alcoholate, in an apolar aprotic solvent in the presence of a phase transfer catalyst.

2. A process according to claim 1 which is carried out in the presence of a sequestering agent.

3. A process according to claim 1, wherein the solvent is an ether, ester, nitrile or aromatic hydrocarbon.

4. A process according to claim 1, wherein the solvent is methyl carbonate.

5. A process according to claim 1, wherein the phase transfer catalyst is a quaternary ammonium salt.

6. A process according to claim 5, wherein the phase transfer catalyst is tetrabutylammonium chloride.

7. A process according to claim 2, wherein the sequestering agent is a crown ether or a compound of formula:

$$N(CH_2CH_2(OCH_2CH_2)_nOCH_3)_3$$

wherein n is 1, 2 or 3.

8. A process according to claim 1, wherein the reaction temperature is from 0° to 100° C.

* * * * *